US011410349B2

(12) United States Patent
Tsui et al.

(10) Patent No.: US 11,410,349 B2
(45) Date of Patent: Aug. 9, 2022

(54) METHODS FOR DATA DRIVEN RESPIRATORY MOTION ESTIMATION

(71) Applicants: KONINKLIJKE PHILIPS N.V., Eindhoven (NL); THE JOHNS HOPKINS UNIVERSITY, Baltimore, MD (US)

(72) Inventors: Benjamin Tsui, Baltimore, MD (US); Patrick Olivier, Solon, OH (US)

(73) Assignees: KONINKLIJKE PHILIPS N.V., Eindhoven (NL); THE JOHNS HOPKINS UNIVERSITY, Baltimore, MD (US)

( * ) Notice: Subject to any disclaimer, the term of this patent is extended or adjusted under 35 U.S.C. 154(b) by 34 days.

(21) Appl. No.: 16/495,924

(22) PCT Filed: Mar. 19, 2018

(86) PCT No.: PCT/EP2018/056779
§ 371 (c)(1),
(2) Date: Sep. 20, 2019

(87) PCT Pub. No.: WO2018/172229
PCT Pub. Date: Sep. 27, 2018

(65) Prior Publication Data
US 2020/0134886 A1  Apr. 30, 2020

Related U.S. Application Data

(60) Provisional application No. 62/575,625, filed on Oct. 23, 2017, provisional application No. 62/476,136, filed on Mar. 24, 2017.

(51) Int. Cl.
*G06T 11/00* (2006.01)
*A61B 5/08* (2006.01)
*G06T 7/00* (2017.01)

(52) U.S. Cl.
CPC .............. *G06T 11/005* (2013.01); *A61B 5/08* (2013.01); *G06T 7/0012* (2013.01); *G06T 2211/412* (2013.01)

(58) Field of Classification Search
CPC ...... G06T 11/00; G06T 11/005; G06T 11/008; G06T 7/0012; G06T 7/00; G06T 7/20;
(Continued)

(56) References Cited

U.S. PATENT DOCUMENTS

2008/0273785 A1  11/2008  Kesner
2010/0166274 A1   7/2010  Busch
(Continued)

FOREIGN PATENT DOCUMENTS

JP   2004045318 A    2/2004
WO  2012176114 A1  12/2012

OTHER PUBLICATIONS

Feng, Tao et al: "Real-time data-driven respiratory gating with optimized automatic VOI selection", 2016 IEEE Nuclear Science Symposium, Medical Imaging Conference and Room-Temperature Semiconductor Detector Workshop (NSS/ MIC/RTSD), IEEE, Oct. 29, 2016) (Year: 2016).*

(Continued)

*Primary Examiner* — Vu Le
*Assistant Examiner* — Courtney Joan Nelson (57) ABSTRACT

A respiratory motion estimation method (30) includes reconstructing emission imaging data (22) to generate a reconstructed image (50). The emission imaging data comprises lines of response (LORs) acquired by a positron emission tomography (PET) imaging device or projections acquired by a gamma camera. One or several assessment volumes (66) are defined within the reconstructed images. The emission imaging data are binned into time interval bins based on time stamps of the LORs or projections. A displacement (Continued)

versus time curve (70) is generated by computing, for each time interval bin, a statistical displacement metric of the LORs or projections that both are binned in the time interval bin and intersect the motion assessment volume. The motion assessment volume may be selected to overlap a motion assessment image feature (60) identified in the reconstructed image.

17 Claims, 7 Drawing Sheets

(58) Field of Classification Search
CPC ........... G06T 7/246; G06T 2207/10104; G06T 2207/10072
See application file for complete search history.

(56) References Cited

U.S. PATENT DOCUMENTS

| | | | |
|---|---|---|---|
| 2010/0189324 A1* | 7/2010 | Wollenweber | A61B 5/721 |
| | | | 382/131 |
| 2011/0081068 A1* | 4/2011 | Brinks | G06T 11/005 |
| | | | 382/132 |
| 2011/0116695 A1* | 5/2011 | Wollenweber | A61B 6/5288 |
| | | | 382/131 |
| 2011/0172526 A1* | 7/2011 | Lachaine | A61B 8/54 |
| | | | 600/439 |
| 2012/0230665 A1 | 9/2012 | Okamoto | |
| 2012/0259196 A1 | 10/2012 | Tanaka | |
| 2013/0287278 A1* | 10/2013 | Olivier | G06T 11/005 |
| | | | 382/131 |

OTHER PUBLICATIONS

Feng, Tao et al: "Real-time data-driven rigid motion detection and correction for brain scan with listmode PET", 2016 IEEE Nuclear Science Symposium, Medical Imaging Conference and Room-Temperature Semiconductor Detector Workshop (NSS/ MIC/ RTSD), IEEE, Oct. 29, 2016) (Year: 2016).*
Kesner, Adam Leon et al "Validation of Software Gating: A Practical Technology for Respiratory Motion Correction in PET", Radiology, 2016.
Ganin, Alex et al "Q.Freeze, One Image, Motion Eliminated, Quantitative Consistency, Low Dose" GE Healthcare, 2012.
International Search Report of PCT/EP2018/056779, dated May 30, 2018.
Feng, Tao et al "Real-Time Data-Driven Respiratory Gating with Optimized Automatic VOI Selection", 2016 IEEE Nuclear Science Symposium, Medical Imaging Conf. and Room-Temperature Semiconductor Detector Workshop, Oct. 29, 2016.
Xu, Jiangyan et al "Improved Intrinsic Motion Detection using Time-of-Flight PET", IEEE Transactions on Medical Imaging, vol. 34, No. 10, Oct. 2015.
Feng, Tao et al "Real-Time Data-Driven Rigid Motion Detection and Correction for Brain Scan with Listmode PET", 2016 IEEE Nuclear Science Symposium, Medical Imaging Conf. and Room-Temperature Semiconductor Detector Workshop, Oct. 29, 2016.
Buther, Florian et al "Detection of Respiratory Tumour Motion using Intrinsic List Mode-Driven Gating in Positron Emission Tomograph", European Journal of Nuclear Medicine and Molecular Imaging, vol. 378, No. 12, Jul. 2020, pp. 2315-2327.

* cited by examiner

METHODS FOR DATA DRIVEN RESPIRATORY MOTION ESTIMATION

CROSS-REFERENCE TO PRIOR APPLICATIONS

This application is the U.S. National Phase application under 35 U.S.C. § 371 of International Application No. PCT/EP2018/056779, filed on Mar. 19, 2018, which claims the benefit of U.S. Provisional Patent Application No. 62/476,136, filed Mar. 24, 2017 and U.S. Provisional Patent Application No. 62/575,625, filed Oct. 23, 2017. These applications are hereby incorporated by reference herein.

FIELD

The following relates generally to the medical imaging arts, emission imaging arts, positron emission tomography (PET) imaging arts, single photon emission computed tomography (SPECT) imaging arts, patient monitoring arts, and related arts.

BACKGROUND

In emission imaging, such as positron emission tomography (PET) or single photon emission computed tomography (SPECT), a patient or other imaging subject is administered a radiopharmaceutical designed to preferentially accumulate in a target organ or tissue, and/or to track a body function such as sugar absorption. The radiopharmaceutical includes a radioactive isotope, (e.g. a positron-emitting isotope in PET). The imaging subject is loaded into the imaging device (e.g. a PET scanner for PET imaging, or a gamma camera for SPECT imaging) and emission imaging data are collected and reconstructed, typically using an analytical or an iterative reconstruction algorithm, to generate a reconstructed image. For improved accuracy, an attenuation map of the imaging subject may be provided, for example computed from a transmission x-ray computed tomography (CT) image of the subject, and the attenuation map is used to correct degradation of the reconstructed images by attenuation of the detected radiation (e.g. 511 keV gamma rays in the case of PET) in the body of the imaging subject.

A further source of image degradation is motion of the subject. Volitional motion can be suppressed by the use of subject restraints. However, non-volitional motion, particularly due to respiration and, to a lesser extent, cardiac cycling, cannot be avoided. To limit radiation exposure to the imaging subject, the radiopharmaceutical dose is kept low, and hence an extended emission imaging data acquisition time typically on the order of minutes to tens of minutes is employed to collect enough data for an acceptable signal-to-noise ratio (SNR). Thus, the acquisition time spans a large number of breaths and heart cycles.

Respiratory gating is a known approach for limiting the impact of respiratory motion on emission imaging quality. In this approach, a respiration monitor belt or other respiration monitoring device is attached to the imaging subject during the emission imaging data acquisition. The emission data are binned according to the gating mechanism, and often only the emission data in a desired gating interval (as indicated by the gating mechanism) are reconstructed to generate the reconstructed image. Typically, the end-exhalation phase is chosen for reconstruction as this period between the completion of exhalation in one breath and the start of inhalation in the next breath is quiescent and typically occupies a substantial portion of the respiratory cycle, (e.g. about 60% in some cases). Cardiac gating may be performed in a similar way, (e.g. using an electrocardiograph (ECG) as the cardiac cycling monitor). However, in a cardiac-gated study, the emission data in each gated phase are reconstructed to form a gated cardiac image. The multiple gated cardiac images are subsequently displayed in cine mode to show the motion of the beating heart.

The following discloses new and improved apparatuses and methods.

SUMMARY

In one disclosed aspect, an emission imaging data processing device comprises an electronic processor and a non-transitory storage medium that stores instructions readable and executable by the electronic processor to perform a respiratory motion estimation method. That method includes: reconstructing emission imaging data to generate a reconstructed image wherein the emission imaging data comprises lines of response (LORs) acquired by a positron emission tomography (PET) imaging device or projections acquired by a gamma camera; determining a motion assessment volume spanning a group of voxels using the reconstructed image; binning the acquired emission list-mode data into time interval bins based on time stamps of the LORs or projections; and generating a displacement versus time curve by operations including, for each time interval bin, computing a (statistical) displacement metric of the LORs or projections that both are binned in the time interval bin and intersect (i.e. pass within) the motion assessment volume. The determining of the motion assessment volume using the reconstructed image may include identifying a motion assessment image feature in the reconstructed image and selecting the motion assessment volume to overlap or include the motion assessment image feature.

In another disclosed aspect, a non-transitory storage medium stores instructions readable and executable by an electronic processor to perform a respiratory motion estimation method by processing operations comprising: reconstructing emission imaging data to generate a reconstructed image wherein the emission imaging data comprises lines of response (LORs) acquired by a positron emission tomography (PET) imaging device or projections acquired by a gamma camera; identifying a plurality of candidate image features in the reconstructed image; computing a statistical measure for each candidate image feature; selecting a motion assessment image feature from the plurality of candidate image features based on the computed statistical measures for the candidate image features; and generating a displacement versus time curve representing motion of the motion assessment image feature from the acquired emission list mode data.

In another disclosed aspect, the displacement versus time curve provides the respiratory motion signals that can be used to define the range, number, and magnitude of the amplitude-based respiratory gates. The amplitude-based respiratory gating scheme will be used to obtain respiratory gated reconstructed images at different respiratory phases.

In another disclosed aspect, an emission imaging data processing method is disclosed. The amplitude-based respiratory gating scheme relates directly to the amount of motion blur within each respiratory gate or phase. They provide more accurate motion compensation and effective motion blur reduction in respiratory motion compensation methods.

In another disclosed aspect, an amplitude-based respiratory gating method is applied to a respiratory motion compensation scheme to reduce respiratory motion blur in the reconstructed image. The acquired emission list-mode data are binned into the amplitude-based equal-count bins respiratory gates. They are reconstructed from the LORs or projections within each respiratory gates to form a series of amplitude-based respiratory gated images. A series of motion vector images between adjacent respiratory gated images representing motion of the motion assessment image feature are calculated. The motion vector images are then used to transform the respiratory gated images onto a single reference phase respiratory motion-free image without the respiratory motion blur effect.

In another disclosed aspect, an emission imaging data processing method is disclosed. Emission imaging data are reconstructed to generate a reconstructed image. The emission imaging data comprise lines of response (LORs) acquired by a positron emission tomography (PET) imaging device or projections acquired by a gamma camera. A motion assessment image feature is identified in the reconstructed image. The emission imaging data are binned into time interval bins based on time stamps of the LORs or projections. A displacement versus time curve representing motion of the motion assessment image feature is generated by computing a displacement metric of the motion assessment image feature for each time interval bin.

One advantage resides in providing respiratory gated emission imaging without the use of a respiratory monitor and with improved signal-to-noise ratio (SNR) compared with other gating approaches that do utilize a respiratory monitor.

Another advantage resides in providing respiratory gated emission imaging without the use of a respiratory monitor, which is adaptable to different types of radiopharmaceuticals that distribute differently in the subject's organs and/or tissues.

Another advantage resides in providing respiratory gated emission imaging without the use of a respiratory monitor, which can utilize movement of an organ or other image feature that is not fully within the image field of view.

Another advantage resides in providing respiratory gated emission imaging without the use of a respiratory monitor, which is computationally efficient through reduction of the extent of image reconstruction entailed in generating the gating signal.

Another advantage resides in providing respiratory gated emission imaging without the use of a respiratory monitor, which is computationally efficient by way of using the acquired list mode data directly.

Another advantage resides in the amplitude-based respiratory gating method which relates the amplitude of the respiratory motion to the amount of image blur. As a result the amplitude-based respiratory motion correction is more effective than the widely used time-based or phase-based respiratory motion correction method due to the irregular respiratory motion in terms of both beat-to-beat breathing period and amplitude.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Respiratory (e.g. breathing) motion estimation techniques disclosed herein operate by quantifying motion of an organ, anatomical boundary, or other image feature that serves as the motion assessment image feature. The respiratory motion is quantified by assessing motion of the motion assessment image feature in the acquired emission imaging data. To identify the motion assessment feature, the acquired emission imaging data are reconstructed to generate a reconstructed image, which has some level of blurriness due to respiratory motion of the imaging subject during the acquisition of the emission imaging data, but is sufficient to be used to identify the image assessment feature. Since the reconstructed image is used only for identifying the motion assessment image feature, it is optionally done without performing attenuation correction using an attenuation map, which speeds the reconstruction process and increases the counts, making the feature more detectable. The reconstruction can employ other computational efficiency-enhancing approaches such as reconstructing using a larger voxel size than would be used for reconstructing a clinical image, and/or using an analytical or non-iterative image reconstruction algorithm, (e.g. filtered backprojection).

It is recognized herein that the optimal organ, anatomical boundary, or other image feature of interest for estimating respiratory motion may be different depending upon numerous factors such as the dosage and type of radiopharmaceutical administered to the imaging subject, the delay interval between administration of the radiopharmaceutical and acquisition of the emission imaging data, imaging subject-specific factors such as weight, girth, individualistic anatomical characteristics and/or metabolism, the chosen imaging field of view (FOV), and so forth. In view of this, in some illustrative respiratory motion estimation techniques disclosed herein, a plurality of candidate image features are identified in the (respiratory motion blurred) reconstructed image, (e.g. the heart, liver, and lung in one illustrative example). The feature could also be an abnormality, such as a lesion. A statistical measure is computed for each candidate image feature, such as an average image intensity of the candidate image feature in the reconstructed image and/or a maximum image intensity gradient of the candidate image feature. The motion assessment image feature is then chosen from the plurality of candidate image features based on the computed statistical measures for the candidate image features. For example, the selection may select the candidate image feature with highest average image intensity as this implies substantial data acquired for the candidate image feature making the respiratory motion estimation more accurate.

In further illustrative embodiment examples, the statistical measure is computed for each candidate image feature, such as the center-of-mass and its location, of the candidate image feature within a selected three-dimensional (3-D) volume-of-interest (VOI) in the reconstructed image, and/or the counts within the volume-of-interest as the candidate image feature moves in and out of it. The motion assessment image feature is then chosen from the plurality of candidate image features based on the computed statistical measures for the candidate image features. For example, the candidate image feature is the locations of the center-of-mass of the heart within a volume-of-interest that encompass the entire heart during respiratory motion. The information will then be used to extract the respiratory motion signal. In another example, the candidate image feature is the total counts of a fixed volume-of-interest coving the upper portion of the liver as it moves in and out of the volume-of-interest during respiratory motion.

In some embodiments, after selection of the motion assessment image feature the emission imaging data are binned into successive time interval bins based on time stamps of the lines of response (LORs, for PET imaging) or projections (for SPECT imaging). For example, in some embodiments, after selection of the motion assessment image feature and respiratory motion signal, the emission imaging data are binned into several amplitude-based bins (with equal-count within each bin) that cover the entire extent of the breathing motion amplitude of the entire or a selected portion of the acquired data. The amplitude-based respiratory gates are then used in combination with the extracted respiratory motion signal to group successive time interval bins based on time stamps of the LORs (for PET imaging) or projections (for SPECT imaging) based on their time stamps for image reconstruction into a series of amplitude-based respiratory gated images.

An advantage of this approach is that the displacement versus time curve, or the respiratory signal curve, can be extracted from the acquired emission list-mode data directly in short time intervals without time-consuming image reconstruction. It is computationally efficient and the extracted data have lower statistical noise fluctuations than that extracted from the reconstructed images. As a result, the extracted displacement versus time curve using this approach will be more accurate and precise. For patient datasets with exceptionally lower counts the noise can be reduced by using larger time intervals for the bins, but at the cost of reduced temporal accuracy. There is also a practical limit the time interval bins cannot be made larger than a reasonable fraction of a single breath.

In this approach, the motion assessment volume is determined using the reconstructed image, to span a 3-D group of voxels that encompasses the candidate image feature. The motion assessment volume is preferably chosen to include mostly the moving feature with minimum contribution from non-moving features or background for maximum signal-to-noise ratio. The determination of the optimal motion assessment volume in an efficient and semi-automatic manner with minimum user intervention is an important feature of the approach and will be described in the following. In some embodiments, the motion assessment volume is selected using an automated process.

In some embodiments, the motion assessment volume is not chosen to precisely align with the motion assessment image feature—indeed, in some embodiments no boundary of the motion assessment volume is selected to coincide with any boundary of the motion assessment image feature. In this approach, a displacement versus time curve is generated by operations including, for each time interval bin, computing a displacement metric of the LORs or projections that both are binned in the time interval bin and intersect the motion assessment volume. The displacement metric for each time interval bin is a statistical metric that serves as a surrogate for determining the actual displacement of the motion assessment image feature in each time interval bin.

In some embodiments, the motion assessment volume is not chosen to precisely align with the motion assessment image feature—indeed, in some such embodiments the motion assessment volume is selected to encompass the motion assessment image feature throughout the respiratory motion cycle. In this approach, the motion assessment volume is determined from the reconstructed image that uses all the LORs or projections from the acquired emission imaging data. A displacement versus time curve is generated by operations including, for each time interval bin, computing a displacement metric of the LORs or projections that both are binned in the time interval bin and intersect the motion assessment volume. The displacement metric for each time interval bin is a statistical metric that serves as a surrogate for determining the actual displacement of the motion assessment image feature in each time interval bin.

In some illustrative embodiments, the motion assessment volume is selected to include the entire motion assessment image feature during the respiratory motion cycle within the data acquisition period. In other embodiments, the motion assessment volume is selected to partially overlap the motion assessment image feature, so that the motion assessment image feature (or a portion thereof) moves into and out of the motion assessment volume as the imaging subject breathes. If the radiopharmaceutical has preferentially accumulated in the motion assessment image feature, then in the former case, a statistical metric that tracks the locations of the center of mass of the total counts in the motion assessment volume provides a displacement metric versus time curve that tracks with respiration. In the latter case, the total counts in motion assessment volume will increase while the portion of the motion assessment image feature moves into the motion assessment volume, and will decrease as the motion assessment image feature moves out of the motion assessment volume, thus providing a displacement metric versus time curve that moves cyclically with the respiration cycle.

Other disclosed embodiments include methods to identify and determine the motion assessment volumes that either encompasses the entire motion assessment image feature, or partially overlap the motion assessment image feature, in an efficient manner. Here the maximum intensity gradient is leveraged in combination with the average intensity meeting some minimum threshold to identify the motion assessment image feature from the reconstructed images. A suitable criterion is to determine the motion assessment volume that will allow extraction of the maximum motion signal with minimum background for the highest possible signal to background ratio by minimizing contributions of counts from non-moving parts of the images.

Figure 1:
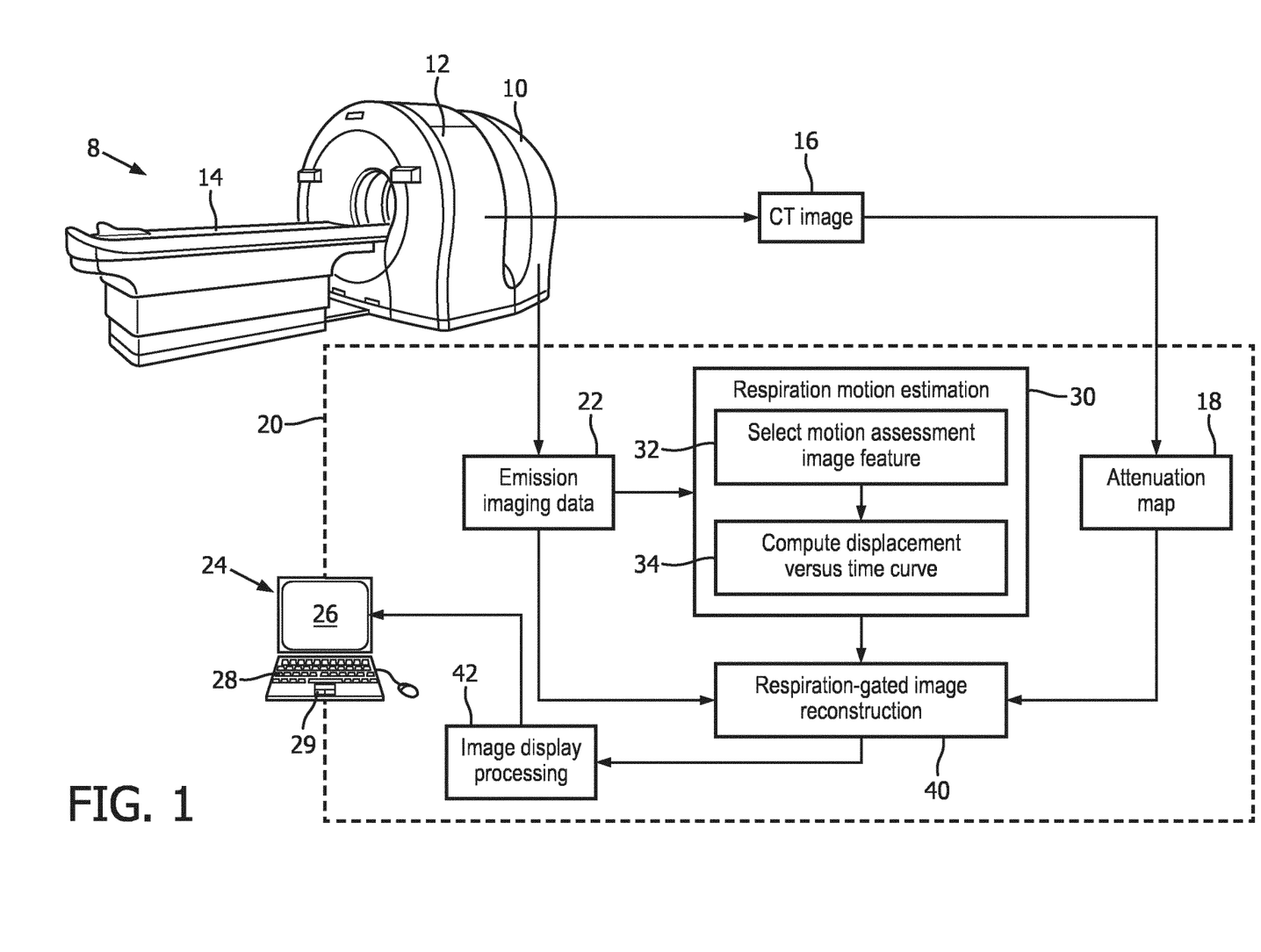
FIG. 1 diagrammatically illustrates an emission imaging system with respiratory gating.

With reference to FIG. 1, an illustrative emission imaging system comprises a combined positron emission tomography (PET)/transmission computed tomography (CT) imaging device 8, which includes both a PET imaging gantry or scanner 10 and a CT gantry or scanner 12 mounted with coaxial bores such that a patient may be loaded onto a common patient table 14 and loaded into either the CT gantry 12 for CT imaging or the PET gantry 10 for PET imaging. The PET imaging gantry or scanner 10 has radiation detectors for detecting 511 keV gamma rays, and a line of response (LOR) is defined by two substantially simultaneous gamma ray detections presumed to originate from a single positron-electron annihilation event. In some embodiments, the radiation detectors of the PET gantry are high-speed detectors which are capable of detecting the time difference between the detections of the two 511 keV gamma rays emitted by a single positron-electron annihilation event. This measured time difference enables further time-of-flight (TOF) localization of the positron-electron annihilation event along the LOR. Each LOR is time stamped with the acquisition time (the finite TOF difference is usually on the order of picoseconds, and for LOR time stamping purposes is negligible). The CT gantry 12, if provided, acquires transmission CT images 16 which may, for example, be used to generate an attenuation map 18 by appropriate conversion of the Hounsfield numbers of the CT image 16 to corresponding absorption values at 511 keV (the energy of gamma rays emitted during positron-electron annihilation events). By way of non-limiting illustrative example, the illustrative PET/CT imaging device imaging scanner 8 may be the PET gantry of a Vereos™ Digital PET/CT scanner, available from Koninklijke Philips N.V., Eindhoven, the Netherlands.

The illustrative emission imaging device is a PET imaging device 10 which acquires emission imaging data in the form of time stamped LORs; in other embodiments the emission imaging device may be a gamma camera which acquires emission imaging data in the form of single photon emission computed tomography (SPECT) projection data. In SPECT imaging, each projection is defined by a single radiation photon detection event, and is again time stamped. As is known in the art, the projections in SPECT imaging are most commonly acquired by one of two large field-of-view gamma cameras, or 2-D planar radiation detectors, mounted on a rotating gantry. The 2-D projection images are formed through the use of a collimator which consists of many long and narrow holes separated by septa made of radiation-absorbing high atomic weight (high Z) material, such as lead or a lead compound, which is mounted on the radiation detector head. The collimator is designed to allow radiation photons that travel in a straight line that is perpendicular to the detection plane or within a narrow angle cone to reach the radiation detector and to form a 2-D projection image. By rotating the gamma cameras around the patient, multiple 2-D projections from different views will be acquired for use in image reconstruction for the final 3-D or multi-slice SPECT images. As with PET imaging, the optional CT gantry 12 can generate a CT image 16 that is converted to an attenuation map 18 for performing attenuation correction during the SPECT reconstruction.

As diagrammatically shown in FIG. 1, an electronic processor 20 processes emission imaging data 22 acquired by the PET imaging gantry or scanner 10 (comprising LORs in the illustrative PET imaging embodiment, or comprising projections acquired by a gamma camera in an alternative SPECT imaging embodiment) to generate respiratory motion estimation and to generate a reconstructed image. The electronic processor 20 may, for example, be embodied as a computer 24 (e.g. a desktop computer, network-based server computer, a dedicated imaging device control computer, various combinations thereof, or so forth) that executes instructions read from one or more non-transitory storage media (e.g. one or more hard drives, optical disks, solid state drives or other electronic digital storage devices, various combinations thereof, or so forth) that stores the instructions. The computer 24 typically includes or has operative access to at least one display 26 (e.g. an LCD display, plasma display, or so forth) for displaying reconstructed images, and optionally also including one or more user input devices such as an illustrative keyboard 28, an illustrative trackpad 29 (or mouse, trackball, touch-sensitive overlay of the display 26, or other pointing device), or so forth.

The emission imaging data 22 is acquired over a relatively extended period, that is, over a time interval encompassing many breaths performed by the imaging subject, in order to provide enough emission imaging data to achieve an acceptable signal to noise ratio (SNR). As diagrammatically indicated in FIG. 1, the electronic processor 20 is programmed by instructions stored on a non-transitory storage medium to perform a respiratory motion estimation process 30 which operates only on the emission imaging data 22. The illustrative respiratory motion estimation process 30 includes an operation or sub-process 32 which selects a motion assessment image feature, and an operation or sub-process 34 which computes a displacement versus time curve representing an estimate of the respiratory motion.

The electronic processor 20 is further programmed by instructions stored on (the same or a different) non-transitory storage medium to perform a respiration-gated image reconstruction process 40 that operates on the emission imaging data 22, the respiratory motion estimation (i.e. displacement versus time curve) output by the process 30, and optionally further on the attenuation map 18 to perform attenuation correction of the reconstructed image. The illustrative respiration-gated image reconstruction process 40 operates to reconstruct a sub-set of the emission imaging data 22 corresponding to a selected respiratory phase (typically end-exhalation, as this phase is quiescent and of long duration) to generate a reconstructed image with reduced blurring due to respiratory motion.

The illustrative electronic processor 20 is further programmed by instructions stored on (the same or a different) non-transitory storage medium to perform image display processing 42 to generate a visualization of the reconstructed image, such as a single two-dimensional (2D) slice image, a 2D maximum intensity projection (MIP), a three-dimensional (3D) rendering of the volumetric reconstructed image, or so forth, which may be displayed on the at least on display 26, and/or stored to a Picture Archiving and Communication System (PACS), and/or printed by a printing device, and/or otherwise utilized.

Figure 2:
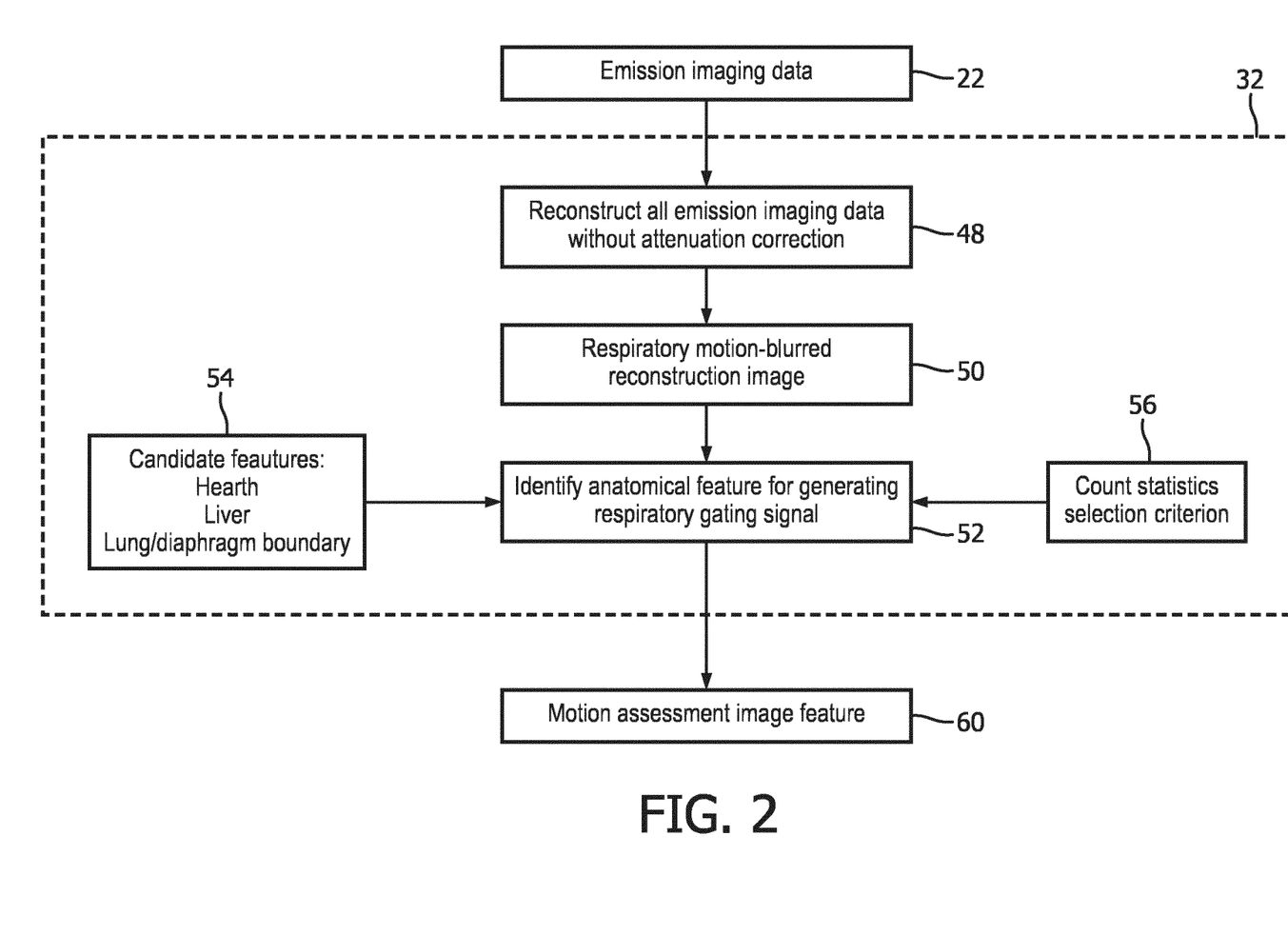
FIGS. 2 and 3 are flow charts, which diagrammatically illustrate the process for performing the respiratory motion estimation of the emission imaging system of FIG. 1.

With continuing reference to FIG. 1 and with further reference to FIG. 2, an illustrative embodiment of the process 32 for selecting a motion assessment image feature is described. In an operation 48, the emission imaging data 22 are reconstructed to generate a reconstructed image 50. In general, all the emission imaging data 22 are reconstructed, thus forming the reconstructed image 50 which is blurred by respiratory motion. The purpose of the reconstructed image 50 is not to provide a clinical image for medical diagnosis or other applications, but merely to provide a way to approximately delineate image features—as such, the image reconstruction operation 48 preferably does not employ attenuation correction using the attenuation map 18, and optionally may use other approaches to achieve a rapid and computationally efficient reconstruction, (e.g. using larger voxel size than would be employed for reconstructing a clinical image, and/or using a non-iterative reconstruction such as filtered backprojection, and/or so forth). (While in the illustrative embodiment the reconstructed image 50 is a single image reconstructed from all the emission imaging data 22, it is alternatively contemplated to generate the reconstructed image 50 comprising a series of reconstructed images, or a reconstructed volume, from the all the emission imaging data or selected portions thereof). In an operation 52, the reconstructed image 50 is used to identify a motion assessment image feature. In some embodiments, a singular pre-selected motion assessment image feature is chosen—for example, if it is known that the radiopharmaceutical preferentially accumulates in the myocardium, then the operation 52 tracks the center of mass of the total counts within a motion assessment volume that encompasses the entire myocardium during the respiratory motion cycles. In another example, if high radiopharmaceutical uptake is found in the liver, a pattern match will be employed to identify the top portion of the liver so as to determine the motion assessment image feature.

In the illustrative embodiment of FIG. 2, however, the goal is to provide a more general process for selecting the motion assessment image feature regardless of the type of imaging that was performed, the type of radiopharmaceutical employed, specifics of the particular imaging subject, and/or so forth. Accordingly, the illustrative selection operation 52 operates to choose an optimal image feature from a set of candidate anatomical features 54, (e.g. the heart, liver, and a lung (or a lung/thoracic diaphragm boundary) in the illustrative example). Each of these anatomical features is characterized using a count statistics selection criterion 56, such as by way of non-limiting illustration an average image intensity or total counts within a motion assessment volume that wholly or partially encompasses the candidate image feature in the reconstructed image 50, or a combination of these. Each candidate image feature is assessed on the basis of the selection criterion 56, and the best image feature for motion estimation as assessed by the selection criterion 56 is chosen as the motion assessment image feature 60. For example, the selection 52 may select the candidate image feature with highest average image intensity as this implies substantial data acquired for the candidate image feature making the respiratory motion estimation more accurate. As another example, the selection 52 may select the optimal motion assessment volume for extracting the highest motion signal with respect to the background from the candidate image feature. The feature extraction methods may suitably utilize the maximum intensity gradient in combination with the average intensity meeting some minimum threshold. This criterion provides the highest motion signal to background ratio by minimizing contributions of counts from non-moving parts of the images.

Figure 3:
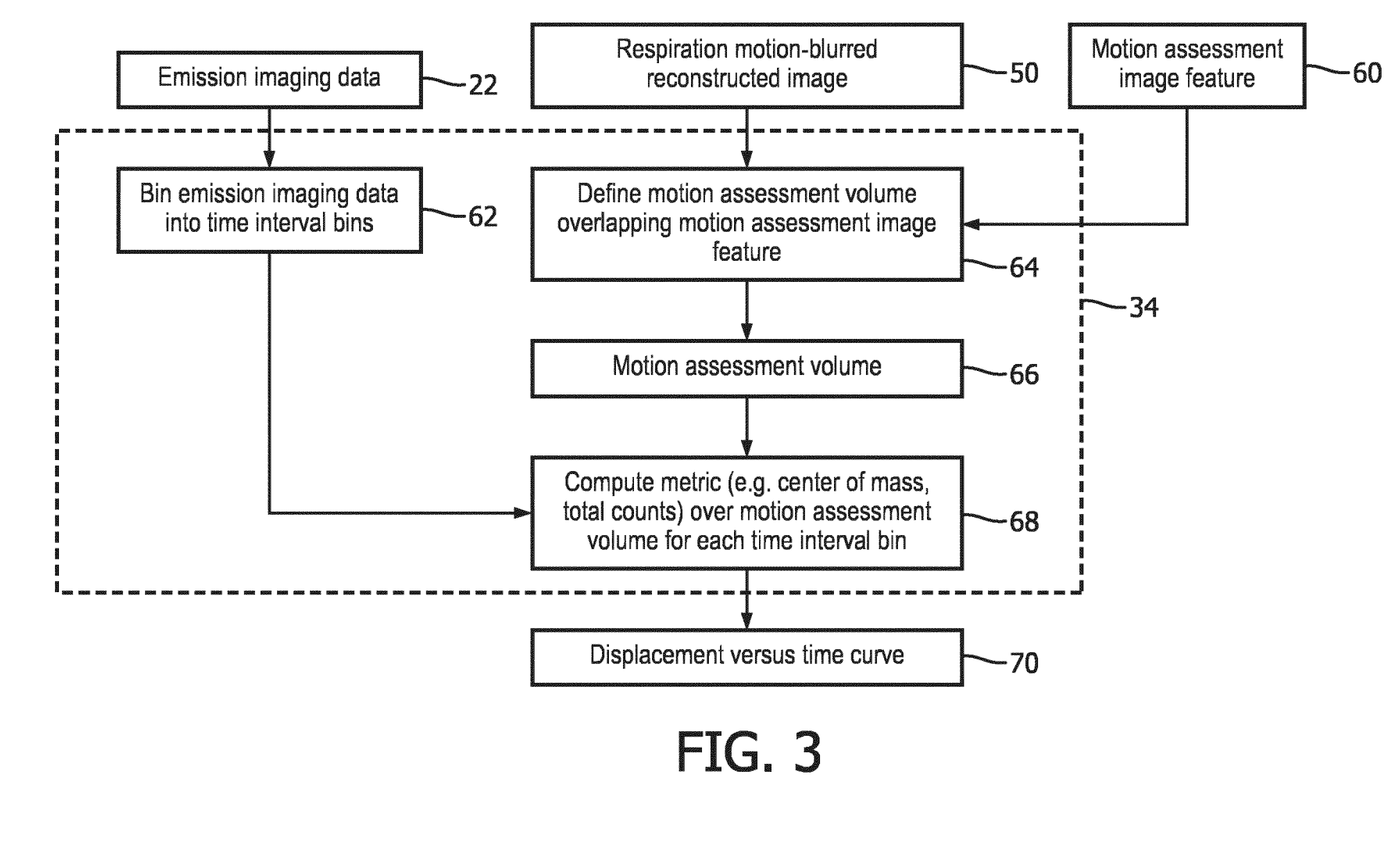

With continuing reference to FIG. 1 and with further reference to FIG. 3, an illustrative embodiment of the process 34 for generating a displacement versus time curve providing respiratory motion estimation is described. In an operation 62, the emission imaging data 22 are binned into time interval bins based on time stamps of the LORs or projections. The time intervals of the bins are chosen to balance temporal resolution (improved by using smaller time intervals) against signal-to-noise ratio (SNR, improved by having more data per bin by using larger time intervals). The time intervals should be small enough so that each time interval is a relatively small fraction of a breath. The goal is to generate a displacement value for each time interval bin, thus creating a displacement versus time curve.

A straightforward approach is to reconstruct the emission imaging data of each time interval bin to generate a corresponding "bin image", and directly measure the displacement of the motion assessment image feature 60 in each bin image. In this case, the displacement metric is not a statistical displacement metric, but rather is a direct measure of the displacement. However, such "bin images" generally suffer from high noise levels. The average adult human takes around 12-20 breaths per minute while at rest, corresponding to one breath every 3-5 seconds, so the time interval bins should have durations generally under one second. In view of this, the amount of data per time interval bin is relatively low, and the reconstructed "bin image" for each time interval bin will have low signal and high noise.

The illustrative process 34 advantageously does not require performing any computationally costly image reconstruction operations, and accordingly is computationally efficient and does not entail processing "bin images" with low SNR. In the illustrative process, in an operation 64 a motion assessment volume 66 is defined, which overlaps the motion assessment image feature 60. The motion assessment volume 66 spans a group of voxels, so as to provide a reasonably high signal value. The motion assessment volume 66 is generally not chosen to precisely align with the motion assessment image feature 60—indeed, in some embodiments no boundary of the motion assessment volume is selected to coincide with any boundary of the motion assessment image feature. Thus, the definition of the motion assessment volume 66 can be made computationally efficient, and does not involve a complex surface delineation or feature segmentation process. For example, in one approach the motion assessment volume 66 is chosen as a standard three-dimensional (3D) shape such as a cylinder or cube positioned to overlap the motion assessment image feature 60. Optionally, the standard shape may be scaled based on a size of the motion assessment image feature 60 to define the motion assessment volume 66. The motion assessment volume 66 may (and in some embodiments preferably does) only partially overlap the motion assessment image feature. With the motion assessment volume 66 defined, an operation 68 is performed in which for each time interval bin, a statistical displacement metric is computed of the LORs or projections that both (i) are binned in the time interval bin and (ii) intersect the motion assessment volume 66. These statistical displacement metrics for successive time interval bins then form a displacement metric versus time curve 70 that serves as a surrogate for determining the actual displacement of the motion assessment image feature in each time interval bin.

Figure 4:
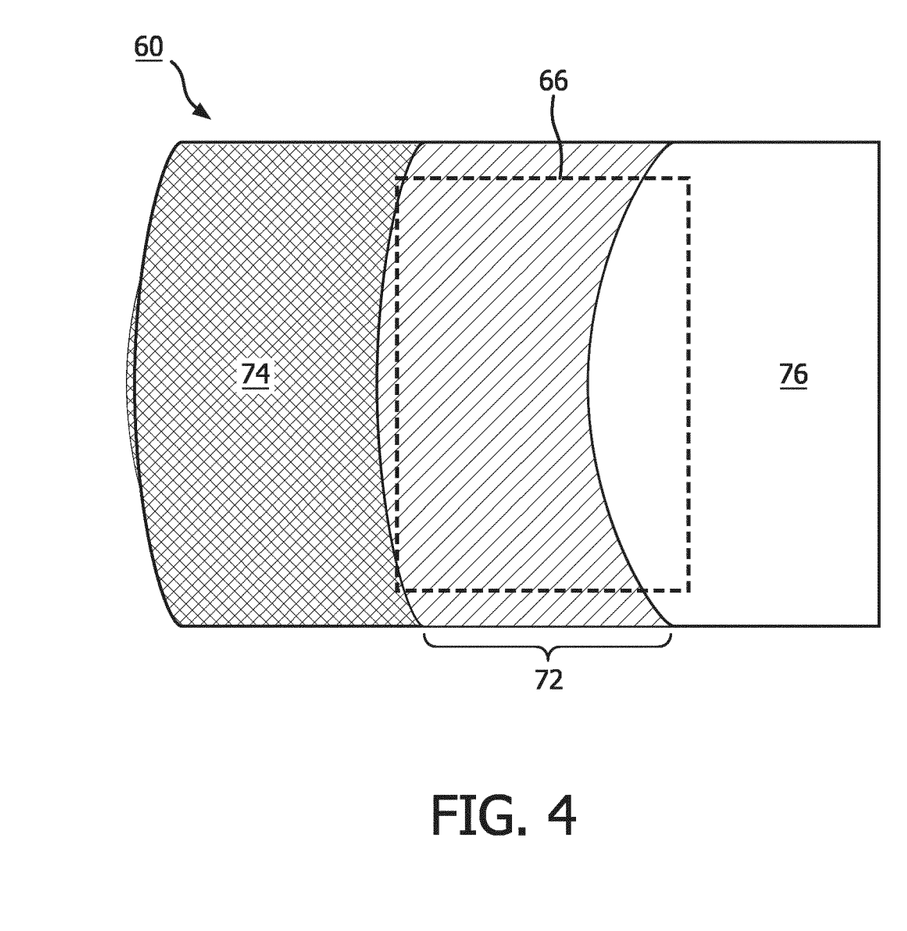
FIG. 4 diagrammatically illustrates a suitable motion assessment volume overlapping a lung/thoracic diaphragm boundary.
Figure 5:
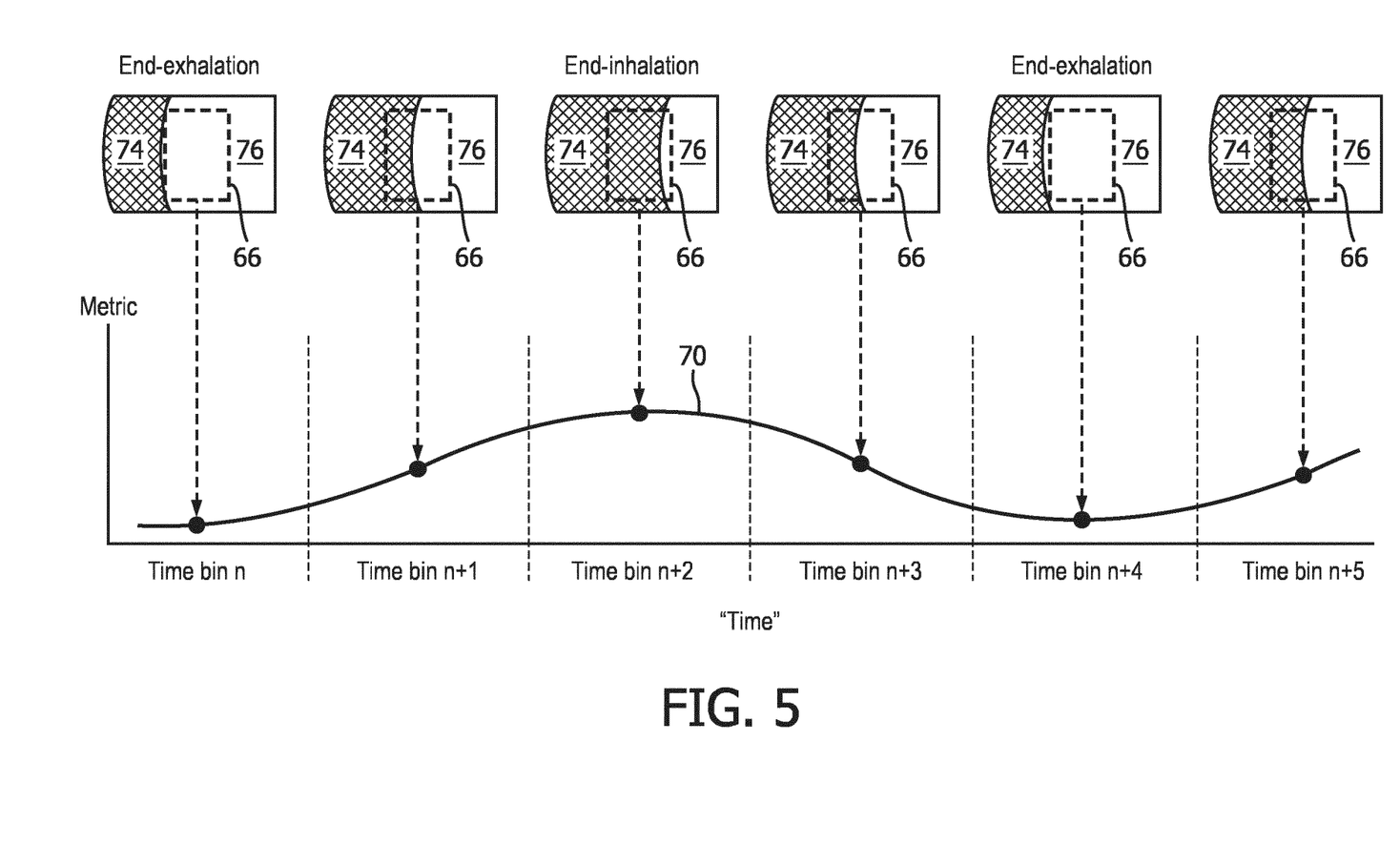
FIG. 5 diagrammatically illustrates generation of a one-dimensional (1D) displacement versus time curve by computing total counts of emission imaging data in the motion assessment volume of FIG. 4 for successive time interval bins.

With reference to FIGS. 4 and 5, an illustrative example of the process 34 depicted in FIG. 3 is described. FIG. 4 illustrates a motion assessment image feature 60 comprising a boundary 72 between a lung 74 and a thoracic diaphragm 76. Because the motion assessment image feature 60 is identified in the respiratory motion-blurred reconstructed image 50, the lung/diaphragm boundary 72 is a blurry boundary, as diagrammatically indicated in FIG. 4 by shading and hatching. Note that in this example it is assumed that the radiopharmaceutical preferentially accumulates in the lung 74 as compared with the thoracic diaphragm 76, and this is diagrammatically indicated in FIG. 4 by darker shading of the lung 74 as compared with the thoracic diaphragm 76. The illustrative motion assessment volume 66 is indicated by a dashed line in FIG. 4, and is a cubic or spherical volume that overlaps the lung/diaphragm boundary 72. FIG. 5 diagrammatically shows the operation 68 of FIG. 3. FIG. 5 plots the results for successive time interval bins denoted "Time bin n", "Time bin n+1", "Time bin n+2", "Time bin n+3", "Time bin n+4", and "Time bin n+5". As labeled at the top of FIG. 5, "Time bin n" and "Time bin n+4" are two successive end-exhalation times, while "Time bin n+2" is an intervening end-inhalation time.

The top row of FIG. 5 shows idealized "bin images" that visualize what would be reconstructed for each time interval bin in the absence of noise (this is not physically realizable due to the low total counts in each time interval bin which would lead to the bin images having low SNR). The motion assessment volume 66 is superimposed on each of these hypothetical idealized bin images. It should be noted that the motion assessment volume 66 is stationary, i.e. is in the same position in space for each hypothetical bin image. In this example, the displacement metric computed for each time interval bin is the total count of LORs or projections that belong to the time interval bin and intersect the motion assessment volume 66. As seen in diagrammatic FIG. 5, at end-exhalation (time interval bins n and n+4) the diaphragm 76 is fully relaxed resulting in the lung deflating to its smallest volume, so that only a small portion (or none) of the lung 74 extends into the motion assessment volume. Since the lung 74 contains a higher concentration of radiopharmaceutical than the diaphragm 76, this results in a low total count as shown in the displacement metric versus time curve at bottom of FIG. 5. (The total count metric is a surrogate for the displacement of the lung/diaphragm boundary—hence this curve is also referred to herein as the displacement metric versus time curve 70). As the imaging subject begins to inhale, the thoracic diaphragm 76 contracts thereby drawing on the lung 74 so as to expand the lung 74, as seen in the hypothetical idealized bin images for time bin intervals n+1, n+5. This moves a greater portion of the lung 74 into the motion assessment volume 66, which increases the total counts in the motion assessment volume 66, causing a rise in the total counts metric as seen in the displacement metric versus time curve 70. At end-inhalation (time interval bin n+2) the lung 74 is maximally extended into the motion assessment volume 66, leading to a peak in the displacement metric versus time curve 70. Thereafter, as the imaging subject begins to exhale (time interval bin n+3) the extension of the lung 74 into the motion assessment volume 66 decreases, leading to a falling portion of the displacement metric versus time curve 70 until it reaches a minimum at end-exhalation.

It should be noted that FIG. 5 is diagrammatic—in particular, the actual duration of the various respiratory phases is not accurately depicted. In an actual resting adult human, the end-exhalation phase is the longest phase, usually occupying around 40% of the total respiratory cycle.

Figure 6:
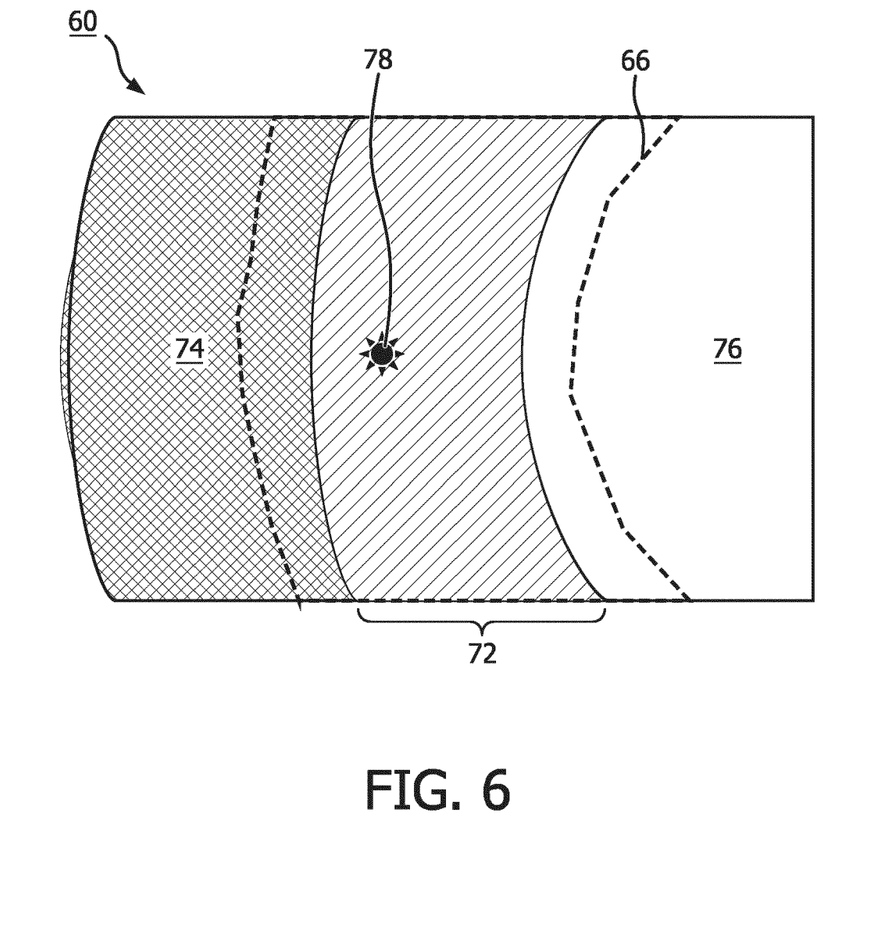
FIG. 6 diagrammatically illustrates another suitable motion assessment volume overlapping or encompassing a lung/thoracic diaphragm boundary.

With reference to FIG. 6, another approach for defining the motion assessment volume 66 is shown, which is well-suited for an implementation of the operation 68 in which the displacement metric is a center-of-mass (COM) of the volume with 'slanted lines' within 66. This example again employs the motion assessment image feature 60 comprising the (respiratory motion-blurred) boundary 72 between the lung 74 and the thoracic diaphragm 76. It is again assumed that the radiopharmaceutical preferentially accumulates in the lung 74 as compared with the thoracic diaphragm 76, and this is again diagrammatically indicated in FIG. 6 by darker shading of the lung 74 as compared with the thoracic diaphragm 76. In this embodiment, the motion assessment volume 66 is defined as follows. The motion-blurred boundary 72 is identified in the reconstructed image 50. This blurred boundary 72 may be identified, for example, as a region of image intensity gradient. The identified blurred boundary 72 is then expanded by some chosen amount (e.g. a certain percentage) to form the motion assessment volume 66 diagrammatically indicated by dashed lines in FIG. 6. In this illustrative example, the displacement metric is a center-of-mass (COM) 78 of the volume with 'slanted lines' indicated in FIG. 6. The COM 78 may be computed, for example, by taking the center point $(x_i, y_i, z_i)$ of each LOR or projection (indexed i) and averaging the center points according to: $x_{COM}=\Sigma_i x_i$; $y_{COM}=\Sigma_i y_i$; and $z_{COM}=\Sigma_i z_i$. However, assuming a prone or supine patient with the z-direction defined as the axial anatomical direction of the patient, the lung is expected to expand "downward" along the axial or z-direction during inhalation and to deflate "upward" along the axial or z-direction during exhalation: accordingly, only the axial component $z_{COM}=\Sigma_i z_i$ is of principle interest, and can serve as the COM value 78. The approach using the COM is particularly effective when the concentration of radiopharmaceutical within the volume with 'slanted lines' is much higher than that in the lung 74 and the thoracic diaphragm 76 volumes.

While the illustrative example leverages the lung/thoracic diaphragm boundary, more generally any organ or tissue can be used that (i) presents a gradient or boundary over which the counts change and (ii) moves in correlation with the respiratory cycle. For example, the motion assessment image feature could be a liver or heart within which the radiopharmaceutical used in the emission imaging preferentially accumulates, and the motion assessment volume is suitably chosen to overlap the heart or liver such that the heart or liver moves into and out of the motion assessment volume in correlation with the respiratory cycle. It will be noted that this approach advantageously can be adapted to situations in which the motion assessment image feature 60 is only partially within the field of view (FOV) of the emission imaging—this is dealt with by selecting the motion assessment volume 66 to overlap and intersect a boundary of the motion assessment image feature 60 that remains fully within the FOV throughout the respiratory cycle.

In a variant approach, the motion assessment volume 66 can be chosen to fully overlap the heart or liver or other motion assessment image feature 60 with some space around the edges. By using center of mass (COM) as the statistical displacement metric, the movement of the heart or liver back and forth within the motion assessment volume 66 in correlation with the respiratory cycle can be tracked. In this variant approach, the motion assessment volume does not intersect a boundary of the motion assessment image feature, but rather the motion assessment volume fully encompasses the motion assessment image feature.

In the example of FIG. 5, the total counts are highest at end-inhalation (time bin n+2) and is lowest at end-exhalation (time bins n and n+4). This results from the particular geometry chosen, in which the higher count lung 74 moves into the motion assessment volume 66 as the imaging subject inhales, and moves out of the motion assessment volume 66 as the imaging subject exhales. For other choices of the motion assessment image feature 60 and the motion assessment volume 66, other relationships may be generated between the respiratory phases (e.g. end-inhalation and end-exhalation) and the statistical displacement metric computed for the motion assessment volume 66. The relationship is readily determined for a given geometry by considering the idealized hypothetical bin images, as illustrated in FIG. 5 for the illustrative example of the lung/diaphragm boundary.

In general, the use of the motion assessment volume 66 chosen to overlap a motion assessment image feature 60 that is optimized to exhibit a strong gradient and/or concentration of radiopharmaceutical enables effective amplification of the SNR by selectively processing emission imaging data contributing to the motion assessment volume 66 which is chosen to be especially sensitive to respiratory motion. A larger motion assessment volume 66 provides more counts to increase signal; while, choosing the motion assessment volume to exclude significant portions of the reconstructed image 50 that do not change with respiration reduces the noise—overall, SNR is amplified. Additionally, by computing a statistical displacement metric for emission imaging data in the motion assessment volume, computationally costly "bin image" reconstruction is avoided. The choice of statistical displacement metric can also be optimized to maximize sensitivity to respiratory motion. For example, in the case of the motion assessment volume 66 totally encompassing the motion assessment image feature 60, a total counts displacement metric may be a poor choice as the total counts will not change if the motion assessment image feature 60 stays entirely within the motion assessment volume 66 throughout the respiratory cycle; whereas, the COM displacement metric may be effective as it tracks the back-and-forth motion of the motion assessment image feature 60 even as it stays entirely within the motion assessment volume 66.

In yet another variant embodiment, it is contemplated to identify the motion assessment volume 66 from the reconstructed image 50 without identifying any particular motion assessment image feature 60. For example, the motion assessment volume 66 may be chosen to be a cylindrical volume or other standard volume positioned at approximately the center of the subject's torso. This approach leverages the expectation that the central torso region contains or borders upon the lungs and diaphragm and hence is likely to exhibit substantial motion correlative with the respiratory cycle. In this case, there is no need to specifically identify the lungs, diaphragm, or lung/diaphragm boundary by segmentation, contouring, or other computationally complex processing.

In the case of PET imaging with time-of-flight (TOF) localization along the LORs, this TOF information may be used to improve the accuracy of the displacement metric used in the operation 68. For TOF-PET, the statistical displacement metric may be computed with weighting of each LOR that intersects the motion assessment volume 66 by a probability that the LOR originated in the motion assessment volume 66, as determined from TOF localization of the LOR. This probability is determined based on how much of the TOF probability distribution along the LOR lies within the motion assessment volume 66, and is analogous to the estimation of the probability that a given LOR with TOF localization originated at a particular voxel in the case of TOF-PET image reconstruction.

The illustrative examples of a suitable motion assessment volume 66 are each a single connected volume. However, it is contemplated for the motion assessment volume 66 to comprise two (or more) volume regions which are separated in space. Said another way, the motion assessment volume 66 may comprise two or more constituent volumes, and in the operation 68 the metric can be different per volume. In such a case, the motion assessment volume 66 comprises two or more constituent volumes and the displacement versus time curve 70 is generated by operations including, for each time interval bin, computing a statistical displacement metric for each constituent volume and combining (e.g. adding together, or averaging) the statistical displacement metrics for the constituent volumes.

Figure 7:
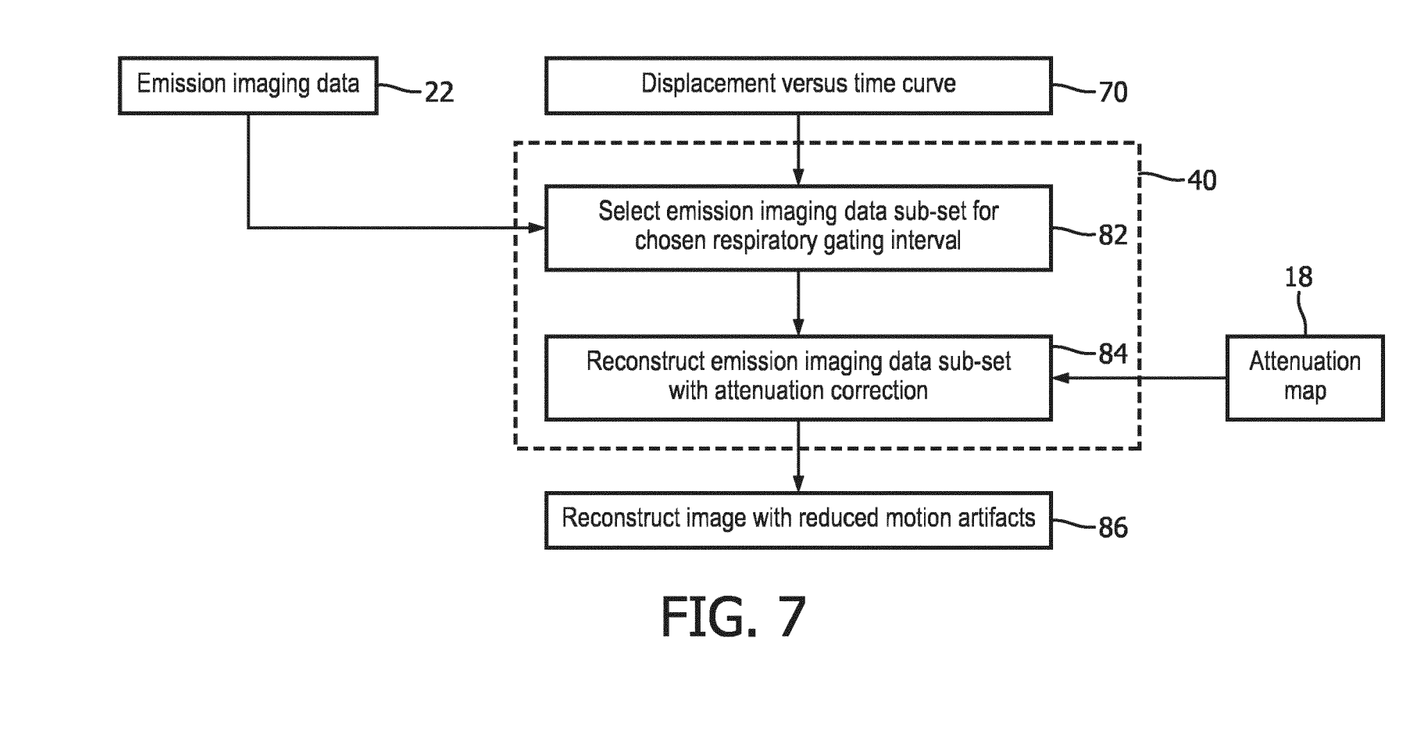
FIG. 7 is a flow chart, which diagrammatically illustrates the process for performing the respiration-gated image reconstruction of the emission imaging system of FIG. 1.

With returning reference to FIG. 1 and with further reference to FIG. 7, an illustrative embodiment of the respiration-gated image reconstruction process 40 is described. In an operation 82, an emission imaging data sub-set is selected from the emission imaging data 22 which corresponds to a specific respiratory phase (or more generally, gating interval). Typically, the respiratory phase chosen for reconstruction is the end-exhalation phase as this is the longest quiescent phase of the respiratory cycle; however, another phase could be chosen. Note that the selected emission imaging data sub-set will generally include a large number of time interval bins from successive respiratory cycles—for example, the end-exhalation phase for the example of FIG. 5 would include (i.e. combine) the emission imaging data in time interval bins n and n+4 as both of these time bins correspond to end-exhalation. In practice, due to the extended length of the physiological end-exhalation phase it is likely that several contiguous time interval bins may correspond to each end-exhalation period and hence be combined in the operation 82. In an operation 84, the phase-specific emission imaging data sub-set is reconstructed. The image reconstruction operation 84 is intended to generate a high-quality reconstructed image suitable for tasks such as clinical diagnosis or clinical evaluation—hence, the image reconstruction operation 84 is preferably performed with attenuation correction using the attenuation map 18, and preferably uses an image reconstruction algorithm that is expected to suppress image artifacts or other image deficiencies. For example, the image reconstruction 84 may employ an iterative image reconstruction technique such as maximum likelihood-expectation maximization (ML-EM), ordered-subset expectation-maximization (OS-EM), or so forth, and may optionally include regularization using an edge-preserving noise-suppressing prior, scatter correction, or other known techniques for enhancing image quality. The resulting reconstructed image 86 with reduced respiratory motion artifacts (e.g. reduced blurring due to respiratory motion) is suitably processed by the image display processing 42 and displayed on the display 26 (see FIG. 1).

With returning reference to FIG. 1, the respiratory phase-specific image reconstruction 40 described with reference to FIG. 7 is one illustrative application of the respiratory motion assessment 30. Other applications are contemplated—for example, the displacement versus time curve 70 may be used as input to a motion correction algorithm that spatially shifts LORs or projections of the emission imaging data 22 based on the extent of displacement indicated by the displacement versus time curve 70. In another contemplated application, if the imaging subject is instructed to hold his or her breath during the imaging, the displacement versus time curve 70 may be used to detect time intervals in which the imaging subject failed to follow this instruction—any imaging data identified by the displacement versus time curve 70 as having been acquired while the imaging subject was not holding his or her breath may then be discarded. These are merely illustrative examples.

While described with reference to respiratory motion estimation, it is also contemplated to employ the disclosed techniques for estimating other types of motion, such as motion due to cardiac cycling, or a known commonplace volitional motion such as rotating the head left or right (in the case of brain imaging, for example). In the case of cardiac cycling, the motion assessment image feature 60 may be the heart or aorta or other major artery, for example.

In the case of brain imaging, the motion assessment image feature 60 may be a brain/skull boundary, for example.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An emission imaging data processing device comprising:
   an electronic processor; and
   a non-transitory storage medium storing instructions readable and executable by the electronic processor to perform a respiratory motion estimation method including:
      determining a motion assessment volume by operations including:
         reconstructing emission imaging data to generate a reconstructed image wherein the emission imaging data comprises lines of response (LORs) acquired by a positron emission tomography (PET) imaging device or projections acquired by a gamma camera; and
         determining the motion assessment volume spanning a group of voxels using the reconstructed image;
      performing the respiratory motion estimation using the motion assessment volume by operations including;
         binning the emission imaging data into time interval bins based on time stamps of the LORs or projections; and
         generating a displacement versus time curve by operations including, for each time interval bin, computing a statistical displacement metric of the LORs or projections that both are binned in the time interval bin and intersect the motion assessment volume;
      wherein the operation of generating of the displacement versus time curve does not include performing any image reconstruction operation.

2. The emission imaging data processing device of claim 1 wherein the statistical displacement metric is a total count of the LORs or projections that both are binned in the time interval bin and intersect the motion assessment volume.

3. The emission imaging data processing device of claim 2 wherein the emission imaging data comprises LORs with time of flight (TOF) localization acquired by a TOF PET imaging device and the computing of the statistical displacement metric includes weighting each LOR that intersects the motion assessment volume by a probability, determined from TOF localization of the LOR, that the LOR originated in the motion assessment volume.

4. The emission imaging data processing device of claim 1 wherein the statistical displacement metric is a center-of-mass of the LORs or projections that both are binned in the time interval bin and intersect the motion assessment volume.

5. The emission imaging data processing device of claim 1 wherein the determining of the motion assessment volume using the reconstructed image includes:
   identifying a motion assessment image feature in the reconstructed image; and
   selecting the motion assessment volume to encompass or overlap the motion assessment image feature; wherein no boundary of the motion assessment volume is selected to coincide with any boundary of the motion assessment image feature.

6. The emission imaging data processing device of claim 5 wherein the motion assessment image feature is a lung and the motion assessment volume is selected to be intersected by or at least partially encompass a boundary between the lung and a thoracic diaphragm; wherein the motion assessment volume is selected by expanding the boundary between the lung and the thoracic diaphragm.

7. The emission imaging data processing device of claim 5 wherein the identifying of a motion assessment image feature includes:
   identifying a plurality of candidate image features in the reconstructed image;
   computing a statistical measure for each candidate image feature; and
   selecting the motion assessment image feature from the plurality of candidate image features based on the computed statistical measures for the candidate image features.

8. The emission imaging data processing device of claim 7 wherein the statistical measure for each candidate image feature comprises at least one of an average image intensity of the candidate image feature in the reconstructed image and a maximum image intensity gradient of the candidate image feature.

9. The emission imaging data processing device of claim 1 wherein the reconstructing of the emission imaging data to generate the reconstructed image does not use an attenuation map to correct for attenuation.

10. The emission imaging data processing device of claim 9 wherein the non-transitory storage medium further stores instructions readable and executable by the electronic processor to perform a gated image reconstruction process including:
   selecting a sub-set of the emission imaging data corresponding to a respiratory gating interval using the displacement versus time curve generated by the respiratory motion estimation method and the time stamps of the LORs or projections; and
   reconstructing the sub-set of the emission imaging data corresponding to the respiratory gating interval to generate a reconstructed image corresponding to the respiratory gating interval.

11. The emission imaging data processing device of claim 10 wherein the reconstructing of the sub-set of the emission imaging data corresponding to the respiratory gating interval to generate the reconstructed image corresponding to the respiratory gating interval includes performing attenuation correction using an attenuation map.

12. An emission imaging device comprising:
   a positron emission tomography (PET) imaging device or a gamma camera configured to acquire the emission imaging data;
   an emission imaging data processing device as set forth in claim 10; and
   a display operatively connected with the emission imaging data processing device to display the reconstructed image corresponding to the respiratory gating interval.

13. The emission imaging data processing device of claim 1 wherein the motion assessment volume comprises two or more constituent volumes and the displacement versus time curve is generated by operations including, for each time interval bin, computing a statistical displacement metric for each constituent volume and combining the statistical displacement metrics for the constituent volumes.

14. A non-transitory storage medium storing instructions readable and executable by an electronic processor to perform a respiratory motion estimation method by processing operations comprising:

reconstructing emission imaging data to generate a reconstructed image wherein the emission imaging data comprises lines of response (LORs) acquired by a positron emission tomography (PET) imaging device or projections acquired by a gamma camera;

identifying a plurality of candidate image features in the reconstructed image;

computing a statistical measure for each candidate image feature;

selecting a motion assessment image feature from the plurality of candidate image features based on the computed statistical measures for the candidate image features;

selecting a motion assessment volume to encompass or overlap the motion assessment image feature, wherein no boundary of the motion assessment volume is selected to coincide with any boundary of the motion assessment image feature; and     generating a displacement versus time curve representing motion of the motion assessment image feature from the emission imaging data and using the motion assessment volume.

15. The non-transitory storage medium of claim 14 wherein the generating of the displacement versus time curve includes:

binning the emission imaging data into time interval bins based on time stamps of the LORs or projections; and     computing a displacement metric of the motion assessment image feature for each time interval bin as a statistical displacement metric of the LORs or projections that both are binned in the time interval bin and intersect the motion assessment volume.

16. An emission imaging data processing method comprising:

reconstructing emission imaging data to generate a reconstructed image wherein the emission imaging data comprises lines of response (LORs) acquired by a positron emission tomography (PET) imaging device or projections acquired by a gamma camera;

identifying a motion assessment image feature in the reconstructed image;

selecting a stationary motion assessment volume that overlaps or encompasses the motion assessment image feature, the stationary motion assessment volume spanning a group of voxels of the reconstructed image;

binning the emission imaging data into time interval bins based on time stamps of the LORs or projections; and     generating a displacement versus time curve representing motion of the motion assessment image feature by for each time interval bin, computing a statistical displacement metric of the LORs or projections that both are binned in the time interval bin and intersect the stationary motion assessment volume;

Wherein the stationary motion assessment volume is in the same position in space for computing the statistical displacement metric of each time interval bin.

17. The emission imaging data processing method of claim 16 wherein the displacement metric of the motion assessment image feature is computed as a statistical displacement metric for each time interval bin without performing any image reconstruction operation.

\* \* \* \* \*